United States Patent [19]

Diebold et al.

[11] Patent Number: 4,764,627
[45] Date of Patent: Aug. 16, 1988

[54] PROCESS FOR PRODUCING FURAN FROM FURFURAL ALDEHYDE

[75] Inventors: James P. Diebold; Robert J. Evans, both of Lakewood, Colo.

[73] Assignee: The United States of America as represented by the United States Department of Energy, Washington, D.C.

[21] Appl. No.: 34,358

[22] Filed: Apr. 6, 1987

[51] Int. Cl.$^4$ ............................................. C07D 307/06
[52] U.S. Cl. ....................................... 549/505; 549/506
[58] Field of Search ................................. 549/505, 506

[56] References Cited

U.S. PATENT DOCUMENTS 3,223,714 12/1965 Manly et al. ......................... 549/506
3,907,915 9/1975 Chang et al. ..................... 260/668 R
3,998,898 12/1976 Chang et al. ..................... 260/668 R

OTHER PUBLICATIONS

Dao et al., Two-Stage Biomass Liquefaction Process, Proceedings of the Nineth Biennial Congress of the International Solar Energy Society, Montreal, Canada, Jun. 23–29, 1985, pp. 1812–1816.

Chen et al., Chemtech, Aug. 1986, pp. 506–511.

Hanniff et al., Conversion of Biomass Carbohydrates into Hydrocarbon Products, Proceedings of IGT/C-BETS Conference on Energy from Biomass and Wastes X, Washington, D.C., Apr. 7–10, 1986.

*Primary Examiner*—Richard L. Raymond
*Attorney, Agent, or Firm*—Kenneth Richardson; James W. Weinberger; Judson R. Hightower

[57] ABSTRACT

A process of producing furan and derivatives thereof is disclosed. The process includes generating furfural aldehyde vapors and then passing those vapors over a zeolite catalyst at a temperature and for a residence time effective to decarbonylate the furfural aldehydes to form furans and derivatives thereof. The resultant furan vapors and derivatives are then separated. In a preferred form, the furfural aldehyde vapors are generated during the process of converting biomass materials to liquid and gaseous fuels.

28 Claims, No Drawings

PROCESS FOR PRODUCING FURAN FROM FURFURAL ALDEHYDE

CONTRACTUAL ORIGIN OF THE INVENTION

The United States Government has rights in this invention under Contract No. DE-AC02-83CH10093 between the U.S. Department of Energy and the Solar Energy Research Institute, a Division of the Midwest Research Institute.

BACKGROUND OF THE INVENTION

1. Field of the Invention

This invention relates generally to the production of furan and, more particularly, to a novel process for converting furfural aldehydes to furan. Specifically, the process of the present invention relates to an improved process for converting furfural corresponding derivatives, which furfural aldehyde and its derivatives are in turn byproducts of the conversion of biomass materials to methanol, gasoline and other fuels.

2. Description of the Prior Art

The conversion of renewable resources, such as biomass and organic wastes, to conventional liquid and gaseous fuels has been approached from several perspectives. One approach includes the fermentation of sugars to ethanol, although this process leaves the lignin and usually the hemicelluloses as byproducts. Another approach includes the complete gasification of biomass to a syngas containing carbon monoxide and hydrogen, followed by the catalytic conversion to alcohol and/or hydrocarbons. While the process is technically feasible, it requires high vapor pressures. Other procedures include pyrolysis and acid hydrolysis of various solid biomass materials to liquid and gaseous fuels.

One of the byproducts of such processes in the wood-to-ethanol conversion as well as other related biomass conversions is the production of furfural aldehydes and derivatives thereof. In order to maximize the economics of such processes, it is highly desirable to be able to convert such byproducts to useful materials.

Furfural aldehyde and its derivatives so produced from biomass conversion have generally had limited uses in the past. However, one potentially important use is in the production of furan and its various derivatives, which in turn have significant potential as octane enhancers and boosters in various gasoline blends. In particular, methylated furans have particularly high blending octane numbers making them especially useful and ecoomic products. In general, the conversion of furfural aldehyde and its derivatives to furan and its counterpart derivatives has been achieved utilizing a variety of existing commercial processes. These processes include a variety of catalytic techniques which, unfortunately, have several drawbacks. In particular, these techniques generally utilize a transition or noble metal catalyst which either produces low yields of furan and furan derivatives or is highly expensive to use due to either the high costs of obtaining the catalyst or of rejuvenating the catalyst for reuse.

A more recent catalytic development for the conversion of furfural aldehyde to furan includes the use of a palladium catalyst on a basic support such as barium sulfate or alumina. This particular process, which is disclosed in U.S. Pat. No. 3,223,714, also requires the use of a dry furfural as a feedstock. This aspect requires an extra purification step and therefore increases the costs associated with this conversion technique. It should be noted that one of the embodiments of this patent includes the use of palladium on a silica-alumina catalyst base, although the actual catalyst itself is the palladium while the silica-alumina functions merely as a structural support. However, when the palladium on such a base is utilized in an acid environment, the catalyst is found to have no activity.

The use of a silica-alumina, or zeolite, catalyst has become very widespread for many different process applications. In particular, the use of a medium pore size zeolite, ZSM-5, has been studied with a wide variety of feedstocks. Typically, however, ZSM-5 is well-known to be an acidic catalyst and therefore highly inappropriate for selective deoxygenation to decarbonylate furfural aldehydes while retaining the ring oxygen. A paper entitled, "Conversion of Biomass Carbohydrates into Hydrocarbon Products" by H. Hanniff, et al., was presented at the IGT/CBETS Conference on "Energy from Biomass and Wastes X" in Washington, D.C., Apr. 7–10, 1986. This paper disclosed, among other items, that furfural can be converted to furan using an HZSM-5 catalyst and resulted in a conversion efficiency of up to 50%. However, higher conversion efficiencies were not reported. Moreover, when the authors co-fed methanol with the furfural, very low yeilds of oxygenated compounds were produced, and neither methyl furan nor any other form of methylated furan was produced. In fact, this particular disclosure teaches that methanol, when added to furfural aldehyde, aids in the destruction of the furan moiety. Thus, there remains a need for an efficient and economic catalytic process for high-efficiency conversion of furfural aldehydes to furans and in particular methylated furans in conjunction with the overall process for converting biomass materials to liquid and gaseous fuel products.

SUMMARY OF THE INVENTION

Accordingly, it is one object of the present invention to provide a process for producing furans and derivatives thereof.

It is another object of the presetn invention to provide a process of converting furfural aldehyde and derivatives thereof to furan and its derivatives utilizing zeolite catalysts.

A further object of the present invention is to provide a process for converting the furfural aldehyde byproducts of biomass-to-fuel conversion procedures to furans and derivatives thereof in high efficiencies utilizing zeolite catalysts.

Yet another object of the present invention is to provide a process for enhancing the economics of biomass-to-fuel conversion techniques by converting furfural aldehyde byproducts to furan and derivatives thereof useful as octane-blending agents.

To achieve the foregoing and other objects and in accordance with the present invention, a process is provided for producing furan and derivatives thereof. Furfural aldehyde vapors are generated and then passed over a zeolite catalyst at a temperature and for a residence time effective to decarbonylate the furfural aldehydes to produce furan and its derivatives. The resultant furan and furan derivative vapors are then separated. In one particular embodiment of the invention, the furfural aldehyde vapors are produced from the conversion of biomass materials to gaseous and liquid fuels. Another preferred embodiment of the invention includes the process whereby the furfural aldehydes are methylated so as to enhance the yield and production of methylated furan derivatives.

DETAILED DESCRIPTION OF THE PREFERRED EMBODIMENTS

As indicated above, furfural aldehyde is a standard reaction byproduct in the conversion of wood or other biomass materials to gaseous and liquid fuels. Further details of such processes are well known to the art and as such will not be repeated in detail. To date, furfural aldehyde has been generally considered an expendable or uneconomically productive byproduct of such processes since existing techniques available for converting such furfural aldehyde byproducts to useful materials are expensive. An economically useful product, however, which may be derived from furfural aldehyde is furan and its derivatives.

Furan is an oxygenated, volatile liquid that has an empirical formula of $C_4H_4O$ and a molecular weight of 68.08. It is a cyclic, unsaturated ether and has the volatility of a hydrocarbn having about the same molecular weight, e.g., 2-methyl-1-butene. Although furan is oxygenated, it is relatively nonpolar and therefore insoluble in water and soluble in hydrocarbons. Likewise, methyl furan is also similar and has a molecular weight of 82.10.

It was discovered that furan and its derivatives, including various methylated furans, may be readily produced by the conversion of furfural aldehyde and its derivatives through the use of a zeolite catalyst of appropriate porosity. Such conversions were obtained at efficiencies of 90-100% if appropriate residence time, temperature and pressure ranges,a nd weight hourly space velocity (WHSV) ratios were observed while passing the furfural aldehyde vapors over the zeolite catalyst. Thus, almost double the previously known conversion efficiency of furfural aldehyde to furan was achieved utilizing zeolite catalysts. Moreover, the conversion of methylated furfural aldehydes to methylated furans utilizing zeolites was simultaneously achieved which heretofore was unknown and unexpected.

More specifically, the zeolite catalysts utilizable in the present invention is preferably a crystalline aluminasilica zeolite catalyst of moderate porosity. The preferred catalyst is the ZSM-5 catalyst described and claimed in U.S. Pat. No. 3,702,886. However, it is envisioned that any zeolite catalyst capable of achieving the apropriate conversion of furfural aldehyde to furan may be utilized in the present invention.

The preferred temperature range maintained during the exposure of furfural aldehyde tot he zeolite catalyst is preferably in the range of 350°-550° C., and more particularly the preferred range is about 450°-500° C. In conjunction with this temperature, the pressure range of the furfural aldehyde vapors over the catalyst is generally in the range of 0.01-20 atmospheres and is preferably about one atmosphere. This is substantially unlike prior catalytic reactions to form furans, which reactions occurred at substantially elevated pressure ranges utilzing expensive catalysts.

The residence time of the vapors over the catalyst as well as the weight hourly space velocity (WHSV) ratios are important parameters in differentiating the process of the present invention from other known processes. The residence time of the present invention wherein the furfural aldehyde vapors are exposed to the ZSM-5 zeolite catalyst preferably varies between approximately 0.1-10 seconds and is most preferably about 1 second. Moreover, the WHSV, which is defined as the ratio of the weight of the injected vapor feed per hour over the weight of the catalyst, may vary from 4-38. The preferred range is about 18-38, which provides a very fast reaction rate and almost 100% conversion efficiency while avoiding the production of hydrocarbons and coke. The previously described Hanniff process, however, includes a WHSV ratio of only approximately 0.3 which results in high coke production as well as furfural decomposition to hydrocarbons. it should be noted, however, that merely increasing the reaction time will not necessarily increase conversion efficiencies correspondingly, since this cannot explain why the present invention efficiently and effectively converts 90-100% methylated furfural aldehyde to methyl furan while the Hanniff process does not convert methylated furfural aldehyde at all. While the various parameters described above are believed to provide some basis for this substantial difference in conversion efficiencies, all aspects which explain these differences are not yet known.

The furfural aldehyde vapor may be passed across the zeolite catalyst in pure form or it may be diluted with an inert carrier gass. Such carrier gases can include, but are not limited to, hydrogen, carbon monoxide, carbon dioxide, methane, helium, argon, nitrogen and/or steam. Moreover, these inert carrier gases mayb e utilized with furfural aldehyde or furfural aldehyde derivatives including methylated derivatives thereof. With respect to such derivatives, the process of the present invention is just as efficient in the conversion of various derivatives of furfural aldehyde, and in particular methylated derivatives such as methylfurfural aldehyde, dimethylfurfural aldehyde, and trimethylfurfural aldehyde. Any one or a mixture of all of these derivatives may be exposed inv apor form to the ZSM-5 zeolite catalyst to form methylated derivatives of furan, and in particular methylfuran, dimethylfuran, trimethylfuran and tetramethylfuran.

Such methylated furan derivatives are more highly desirable end products than pure furan in terms of ther use as octane boosters since methylated furan has a much higher octane number than pure furan. One means of methylating the furfural aldehyde to produce methylated furan is to cofeed methanol with furfural aldehyde, which cofeeding methylates the furfural aldehyde and thereby produces methyl furan after exposure thereof to the zeolite catalyst at the appropriate temperature, pressure, residence time and WHSV ratio. It is also envisioned that the present invention may be utilized to produce ethylated furans by cofeeding ethanol with the furfural aldehyde rather than methanol. It is further understood that other materials may be cofed with the furfural aldehyde to produce higher molecular weight products. Examples of such cofeed materials include, but are not limited to, acetic acid, acetaldehyde, propionaldehyde, acetone, acrolein, dimethyl ether, methylal, and/or any mixture of these materials.

As previously indicated, one of the purposes of converting furfual aldehyde is to economically utilize the furfural aldehyde byproduct stream of a biomass-to-liquid and gaseous fuel production process. A preferred biomass conversion process scheme includes either the pyrolysis or the acid hydrolysis of cellulose, hemicellulose, lignon and lignocellulosic materials such as biomass or municipal solid wastes, to various gaseous and liquid fuel materials such as gasoline, methanol and the like. Due to the fact that such pyrolysis and acid hydrolysis techniques are likely to produce furfural aldehyde feeds which contain organic impurities, the process of the present invention can be utilized to convert such organic impurities as well as the furfural aldehyde to furan derivatives thereof as impurities. Such organic impurities or derivatives thereof can be readily separated from the furan and furan derivatives by any known distillation or other state of the art technique. Further discussion of such distillation and other technique is not deemed necessary as these procedures are well known in the art and are readily available to anyone skilled in the art.

Once the furan and furan derivatives are produced through the use of the present invention, they may be incorporated with or without further purification into gasoline or other fuel products as octane boosters and additives to enhance the combustion capability of such fuels. This is due to the fact that impure mixtures of product furans and hydrocarbons may be used as high octane blending stocks which command a higher price than pure gasoline due to the high blending octane value and excellent solubility of furan and furan derivatives in hydrocarbons. Thus, the production of high octane blending agents such as furan and furan derivatives from previously uneconomic byproduct streams of furfural aldehyde in the biomass to fuel production scheme is a highly desirable and economic technique.

Examples of more specific conversions using the process of the present invention are illustrated in the Examples provided below.

EXAMPLE I

A small sample of cellulose power (Avicel PH-103) was pyrolyzed, and the vapors which were diluted with helium were immediately passed over a ZSM-5 catalyst. The products were analyzed directly by a molecular-beam mass spectrometer (MB-MS). With the cellulose derived vapors passed over the catalyst, a vary changed slate of product spectra were observed as compared to the uncatalyzed case, indicative of a very high reactivity with the catalyst. Except for the absence of dimethyl ether, this product spectra had a very great similarity to the complex mixture of hydrocarbons obtained from fairly severe reaction with methanol vapors previously tested, except that there were also observed large peaks at mass numbers 68 and 82 which were not seen in the product spectra using pure methanol. These mass numbers were also not seen with the uncatalyzed spectra of cellulose-derived vapors.

When pineflower was pyrolyzed and the vapors passed over the ZSM-5 catalyst the peaks associated with cellulose vapors were missing from the product spectrum and, in addition to the rise of hydrocarbon paraffins and olefins, there were significant peaks at mass numbers 68 and 82.

It was speculated that mass 68 was furan and that mass 82 was methyl furan. An experiment was performed which showed that furan when passed over the ZSM-5 catalyst at these conditions, did not give rise to spectra other than at 68, indicating the refractory nature of furan to this catalyst. This is consistent with the lack of net activity of furan under very mild reaction conditions. Therefore, it was determined that the cellulose powder when pyrolyzed and exposed to the ZSM-5 catalyst produced resultant vapors containing furan and methylfuran.

EXAMPLE II

It was hypothesized that if the proper model compound were selected for reaction over the ZSM-5 catalyst, that furan would be the predominant product. If the spectra were to show a strong peak at m/z 68 without the complex hydrocarbon spectra seen when reacting unsaturated hydrocarbons, then it could be concluded that furan was indeed a product. Among the model compounds evaluated were furfural aldehyde and methyl furfural aldehyde, and these were found to be very reactive over ZSM-5. Specifically, furfural aldehyde vapors were passed over the ZSM-5 catalyst at a temperature of about 450° C. for residence time of about 1 second and was converted almost quantitatively (almost 100 percent) to m/z 68 with small peaks also present at m/z's 39, 40, 28 and 29. These small peaks are characteristic fragment ions of furan. Due to the lack of a complex spectrum associated with cyclopentene and pentatdiene reactions, as well as the specific lack of a peak at m/z 53 (a fragment ion of $C_5H_8$), it was concluded that the peak at m/z 68 was due to furan.

EXAMPLE III

An experiment similar to that of Example II was repeated utilizing 5-methylfurfural aldehyde. The 5-methylfurfural aldehyde was passed over the ZSM-5 catalyst with the same time and temperature conditions as Example II and resulted in a small amount of residual reactant at m/z 110, but major peaks at m/z's 82, 53 and 39. The peaks at m/z's 53 and 39 are characteristic fragment ions from methyl furan. Due to the lack of complex hydrocarbon spectra associated with the reduction of hexadienes or cyclohexene over this catalyst, and the lack of a peak at m/z 67 (a fragment ion of $C_6H_{10}$), it was concluded that 2-methylfuran was being formed from 5-methylfurfural aldehyde.

EXAMPLE IV

Furfural aldehyde and methanol were co-fed in equal amounts over a ZSM-5 zeolite catalyst at atmospheric pressure and at about 500° C. temperature for a residence time of about 1 second. The WHSV ratio was about 25 for each species in the feedstock vapor. The resultant vapor was collected and tested and resulted in a furan/methylfuran/dimethylfuran product ratio of about 5.6/2/1. Therefore, co-feeidng methanol produced substantial methylation of the furan product.

Although the literature describes processes in which furfuryl aldehyde, and in some cases 5-methylfurfural aldehyde, are decarbonylated to from the corresponding furan and methyl furan, these processes were all accomplished in the presence of a transition or a noble metal catalyst and in a basic solution or catalyst support. Since ZSM-5 is well known to be an acidic catalyst, it was highly unexpected that it would act as described above to decarbonylate both furfuryl aldehyde as well as methylated furfural aldehyde derivatives to form furans and methylated furans. In addition, many of the prior art processes to convert furfuryl aldehyde to furan require the use of a dry purified reactant, which is an expensive formation step. This is not necessary when using the process of the present invention. Finally, it was unexpected that the oxygen in the furan molecules would not be susceptible to removal by the ZSM-5 catalyst at the more severe conditions employed in the Examples provided above. Therefore, it is clear that an inexpensive process utilizing a ZSM-5 catalyst and other similar zeolite catalysts has been discovered whereby furfural aldehyde, methylated furfuryl aldehyde and other derivatives thereof, may be readily converted to furan, methylated furans and other derivatives having high octane blending numbers for use in gasoline and other fuel products. Thus, a byproduct of the biomass-to-fuel production, i.e., furfuryl aldehyde, may now be readily converted to a highly useful and economic product which heretofore was previously discarded or utilized in other uneconomic ways.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to within the scope of the invention as defined by the claims which follow.

The embodiments of the invention in which an exclusive property or privilege is claimed are defined as follows:

1. A process for producing furans and derivatives thereof comprising generating furfural vapors, passing said vapors over a zeolite catalyst at a WHSV ratio of about 18–38 in an acidic environment, and at a temperature and for a residence time effective to decarbonylate said furfural to said furans and derivatives thereof, and separating the resultant furan and furan derivative vapors.

2. The process of claim 1, wherein said effective period of time comprises about 0.1–10.0 seconds.

3. The process of claim 2, wherein said effective period of time comprises approximately 1 second.

4. The process of claim 1, wherein said effective temperture comprises approximately 350°–550°C.

5. The process of claim 4, wherein said effective temperature comprises approximately 400°–450° C.

6. The process of claim 1, wherein said vapors are passed over said zeolite catalyst at a pressure of approximately 0.01–20.0 atmospheres.

7. The process of claim 6, wherein said pressure is approximatley atmospheric pressure.

8. The process of claim 1, wherein said zeolite catalyst comprises a crystalline aluminosilica zeolite catalyst of moderate porosity.

9. The process of claim 8, wherein said zeolite catalyst comprises ZSM-5 catalyst.

10. The process of claim 1, wherein said furfural vapors are diluted with an inert carrier gas.

11. The process of claim 10, wherein said inert carrier gas is selected from the group consisting of hydrogen, carbon monoxide, carbon dioxide, methane, helium, argon, nitrogen, and steam.

12. The process of claim 1, wherein said furfural vapors are methylated to form methylated derivatives of furfural to produce methylated furans.

13. The process of claim 1, wherein said furfural vapors comprise at least one member of the group consisting of furfural, methyl furfural, dimethyl furfural, trimethyl furfural, and mixtures thereof.

14. The process of claim 1, wherein said furfural vapors comprise 5-methyl furfural, and wherein said resulting furan vapors comprise 2-methyl furan.

15. The process of claim 1, wherein an alcohol selected from the group consisting of methanol and ethanol is cofed with said furfural vapors to increase the production and yield of the corresponding methylated or ethylated furans.

16. The process as claimed in claim 1, wherein said furfural vapors comprise a mixture of furfural derivatives contaminated with various organic impurities that, when passed over said zeolite catalyst, produce resultant vapors of furan derivatives.

17. The process of claim 16, wherein said organic impurities comprise those materials derived from the pyrolysis or acid hydrolysis of cellulose, hemicellulose, lignin, and lignocellulosic materials comprising biomass and municipal solid wastes.

18. A process of converting furfural and derivatives thereof to furans and derivatives thereof comprising exposing vapors of said furfural and derivatives to a zeolite catalyst in an acidic environment and at a temperature range of approximately 350°–550° C. for 0.1–10 seconds at 0.01–20 atmospheres and with a WHSV ratio of about 18 to 38 to produce vapors of said furans and derivatives, and separating said furans and derivatives from the residual vapor products.

19. The process as claimed in claim 18, wherein said zeolite catalyst comprises a ZSM-5 catalyst.

20. The process as claimed in claim 18, wherein the vapors of said furfural and drivatives thereof are diluted with an inert carrier gas selected from the group consisting of hydrogen, carbon monoxide, carbon dioxide, methane, helium, argon, nitrogen, and steam.

21. The process of claim 18, wherein said furfural derivatives comprise at least one member selected from the group consisting of methylfurfural, dimethylfurfural aldehyde, trimethylfurfural, and wherein said furan derivatives comprise a member selected from the group consisting of methylfuran, dimethylfuran, trimethylfuran, and tetramethylfuran.

22. The process as claimed in claim 18, wherein methanol is cofed with said furfural and derivatives thereof over said zeolite catalyst to increase the yield of methylated furans.

23. The process as claimed in claim 18, wherein said furfural comprises organic impurities derived from the pyrolysis or acid hydrolysis of cellulosic, hemicellulosic, and lignocellulosic materials comprising biomass and municipal solid wastes.

24. In a process for converting biomass materials to liquid and gaseous fuels, the improvement of converting methylated furfural byproducts to furan and derivatives thereof comprising passing the vapors of said furfural byproducts over a zeolite catalyst at a WHSV ratio of about 18–38 in an acidic environment to produce vapors of methyl furan and derivatives thereof.

25. The improvement of claim 24, wherein said zeolite catalyst comprises a ZSM-5 catalyst.

26. The improvement of claim 24, wherein said furfural byproduct vapors are methylated to produce said methylated furfural prior to their exposure to said zeolite catalyst to produce methylated furan derivatives.

27. The improvement of claim 24, wherein methanol is cofed with said vapors of furfural to increase the yield and production of methylated furan derivatives.

28. The improvement of claim 24, wherein said furfural byproducts comprise organic impurities derived from the pyrolysis or acid hydrolysis of said biomass materials comprising cellulose, hemicellulose, lignin and lignocellulosic materials.

* * * * *